(12) United States Patent
Hadley et al.

(10) Patent No.: US 7,613,494 B2
(45) Date of Patent: Nov. 3, 2009

(54) APPARATUS AND METHODS FOR IMAGING USING AN ANATOMICAL POSITIONING SYSTEM

(75) Inventors: J. Rock Hadley, Centerville, UT (US);
Dennis Parker, Centerville, UT (US);
Aaron J. Burnett, Bountiful, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 713 days.

(21) Appl. No.: 10/998,189

(22) Filed: Nov. 26, 2004

(65) Prior Publication Data
US 2005/0165291 A1     Jul. 28, 2005

Related U.S. Application Data

(60) Provisional application No. 60/525,562, filed on Nov. 26, 2003.

(51) Int. Cl.
*A61B 5/05*       (2006.01)
(52) U.S. Cl. ......................................... 600/407; 600/415
(58) Field of Classification Search ...................... 5/600; 600/421, 422, 410; 324/318, 322; 378/16, 378/177; 250/363.02, 491.1
See application file for complete search history.

(56) References Cited

U.S. PATENT DOCUMENTS

| | | | | | |
|---|---|---|---|---|---|
| 4,821,729 | A | * | 4/1989 | Makofski et al. | 600/439 |
| 4,963,903 | A | * | 10/1990 | Cane | 396/428 |
| 5,005,558 | A | * | 4/1991 | Aomori | 600/141 |
| 5,517,120 | A | * | 5/1996 | Misic et al. | 324/318 |
| 5,855,582 | A | * | 1/1999 | Gildenberg | 606/130 |
| 5,916,189 | A | * | 6/1999 | Sullenperger et al. | 602/36 |
| 6,121,953 | A | * | 9/2000 | Walker | 345/156 |
| 6,282,264 | B1 | * | 8/2001 | Smith et al. | 378/189 |
| 6,577,888 | B1 | * | 6/2003 | Chan et al. | 600/422 |
| 6,784,665 | B1 | * | 8/2004 | Chan et al. | 324/318 |
| 6,980,002 | B1 | * | 12/2005 | Petropoulos et al. | 324/318 |
| 2001/0005410 | A1 | * | 6/2001 | Rasche et al. | 378/197 |
| 2002/0106137 | A1 | * | 8/2002 | Chen et al. | 382/321 |
| 2003/0001573 | A1 | * | 1/2003 | Misic | 324/318 |
| 2003/0235265 | A1 | * | 12/2003 | Clinthorne et al. | 378/4 |

* cited by examiner

*Primary Examiner*—Eric F Winakur
*Assistant Examiner*—Lawrence N Laryea
(74) *Attorney, Agent, or Firm*—Thorpe North & Western LLP

(57) ABSTRACT

The present invention includes a system that allows for the easy substitution of imaging elements attached to an anatomical positioning device. One or more imaging elements may be mounted to the anatomical positioning device in such a way that the placement of the imaging elements in relation to the anatomical positioning device and the subject can be easily controlled by the operator.

18 Claims, 12 Drawing Sheets normal bifurcation bifurcation rotated 90° reference data set rotated head data set head rotation: 13° flexion, 18° tilt right, 71° rotate right head rotation: 13° flexion, 18° tilt right, 71° rotate right head rotation: 0.5° flexion, -0.9° tilt left, 2.4° rotate right head rotation: 1.4° flexion, 0.9° tilt right, 1.8° rotate right

APPARATUS AND METHODS FOR IMAGING USING AN ANATOMICAL POSITIONING SYSTEM

CROSS-REFERENCE TO RELATED APPLICATION

Claim of Priority: Pursuant to the provisions of 35 U.S.C. § 119(e), this application claims the benefit of the filing date of provisional patent application Ser. No. 60/525,562, filed Nov. 26, 2003, for "APPARATUS AND METHODS FOR REPEATABLE HEAD AND NECK POSITIONING FOR MAGNETIC RESONANCE IMAGING," the contents of which are incorporated by reference.

GOVERNMENT RIGHTS

The United States government may have rights in the following invention pursuant to a grant from the National Institutes of Health (NIH 57990).

TECHNICAL FIELD

The present invention relates generally to the field of medical devices. More particularly, the present invention relates to medical devices for providing anatomical positioning for medical imaging.

BACKGROUND

Currently known apparatus and techniques for providing anatomical positioning for medical imaging include rigid devices with imaging elements such as non-positionable MRI coils or ultrasound emitters built right into the anatomical positioning device. Where variable positioning of imaging elements has been desired, rolled-up towels and sponges or bean-bag support systems have been used to hold separate imaging elements in position near the area to be imaged. These techniques are seldom reproducible in a consistent manner and create difficulty in achieving optimal imaging element positioning.

In addition to the need for variable element placement that is reproducible, situations occur where the user desires that more than one type of imaging element be used with a specific anatomical positioning device. For example, different imaging elements may be more or less useful given specific subject anatomy. In addition, the operator may require different images using different imaging elements while the subject is to remain in essentially the same position. The currently known apparatus are not believed to allow for multiple interchangeable imaging elements to be used with the same anatomical positioning device. This drawback forces users to purchase and keep on hand multiple anatomical positioning devices for use with the same patient and increases the time required for imaging as different systems are assembled and used for the same patient, which may require multiple sessions.

Furthermore, available anatomical positioning systems are often designed for radiation therapy treatment rather than for imaging purposes. Typically, imaging requires a subject to be positioned within the positioning system for longer periods than are required during radiation treatment. Thus, subject comfort during imaging becomes of greater concern.

FIG. 1 hereof depicts one consequence of acquiring an MRI image of the carotid arteries in the conventional manner. The top image of FIG. 1 depicts an MRI image of normal bifurcation of the carotid artery. The lower image of FIG. 1 depicts how bifurcation of the carotid artery may appear twisted in a traditional image capture attempted using the same system. For treatment of the head and neck, as by performing a procedure based on MRI results or during imaging, this variability is undesirable.

It is thus readily apparent that improvements over known anatomical positioning devices for imaging are needed. A patient positioning and imaging system that provides modular imaging elements which are substitutable would be an improvement in the art. A patient positioning and imaging system which is precisely and variably positionable would similarly constitute an improvement in the art.

SUMMARY

The present invention includes a system that allows for the substitution of imaging elements attached to an anatomical positioning device. One or more imaging elements may be mounted to the anatomical positioning device in such a way that the placement of the imaging elements in relation to the anatomical positioning device and the subject can be easily controlled by the operator.

In a first illustrative embodiment, a system in accordance with the present invention is adapted for small, region-specific dedicated MRI radio frequency coils attached to a system for positioning the head and neck of a subject. Each MRI coil of the exemplary embodiment is attached to the head and neck anatomical positioning device via flexible, postionable, retainable members, such as flex pipe, allowing the MRI coil to be placed in relation to the immobilized head or neck of the subject as the operator desires. In some exemplary embodiments, the coils may be easily replaced with other coils without moving the subject.

The present invention also includes methods of acquiring medical images. In these methods, imaging elements are removably attached to an anatomical positioning device and an operator acquires one or more images using one or more imaging elements which are attached to the anatomical positioning device. The imaging elements may be attached to the anatomical positioning device in such a way that the placement of the imaging elements in relation to the anatomical positioning device and the subject can be easily altered by the operator.

DESCRIPTION OF THE DRAWINGS

It will be appreciated by those of ordinary skill in the art that the elements depicted in the various drawings are not necessarily to scale, but are for illustrative purposes only. The nature of the present invention, as well as other embodiments of the present invention, may be more clearly understood by reference to the following detailed description of the invention, to the appended claims, and to the several drawings.

DETAILED DESCRIPTION

The present invention includes a system which allows for the substitution of imaging elements attached to an anatomical positioning device. The imaging elements are mounted to the anatomical positioning device in such a way that the elements can be replaced without removing or moving the subject. In addition, the imaging elements can be mounted to the anatomical positioning device such that placement of the imaging elements in relation to the subject can be easily controlled by the operator.

Figure 1:
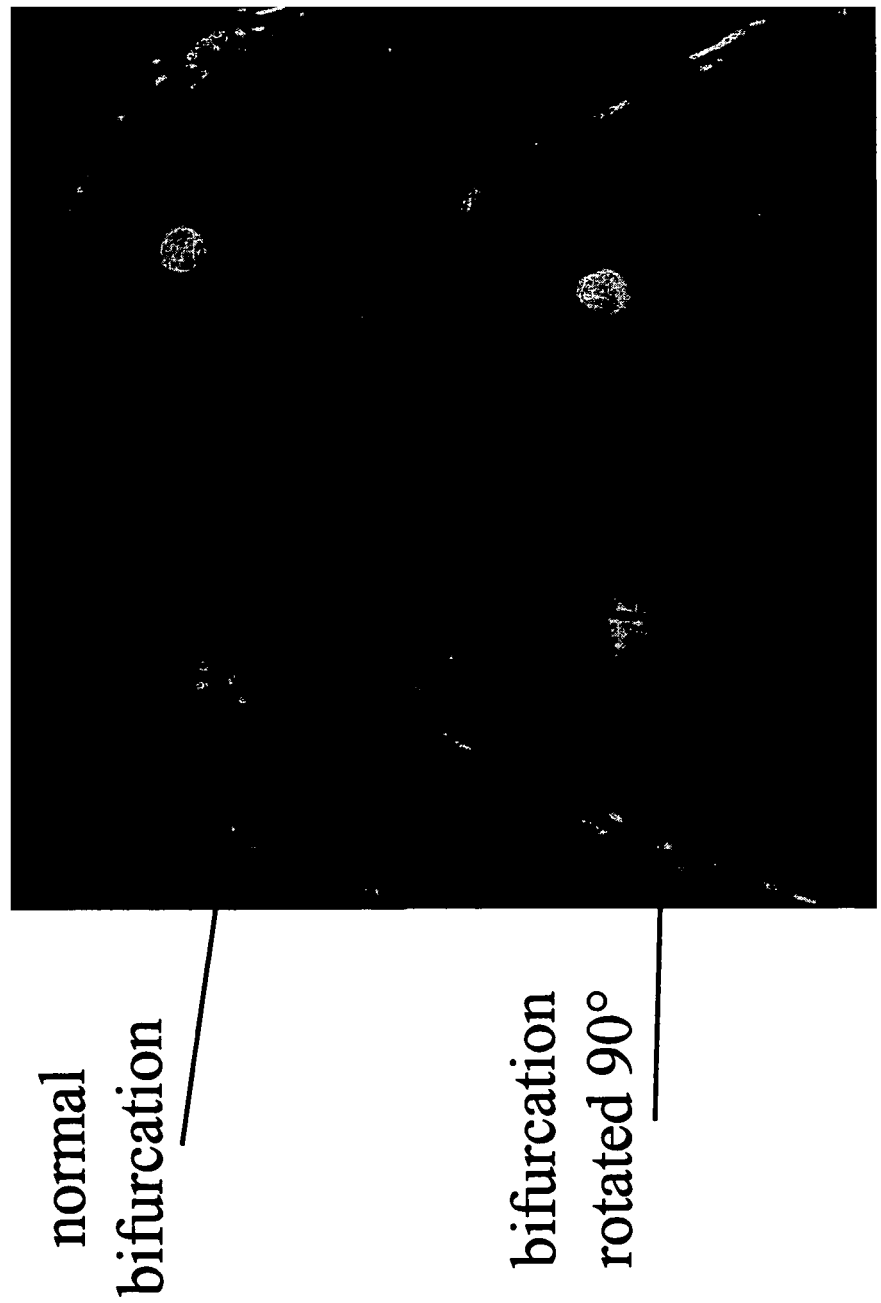
FIG. 1 depicts possible consequences of obtaining an MRI image in the traditional manner.
Figure 2:
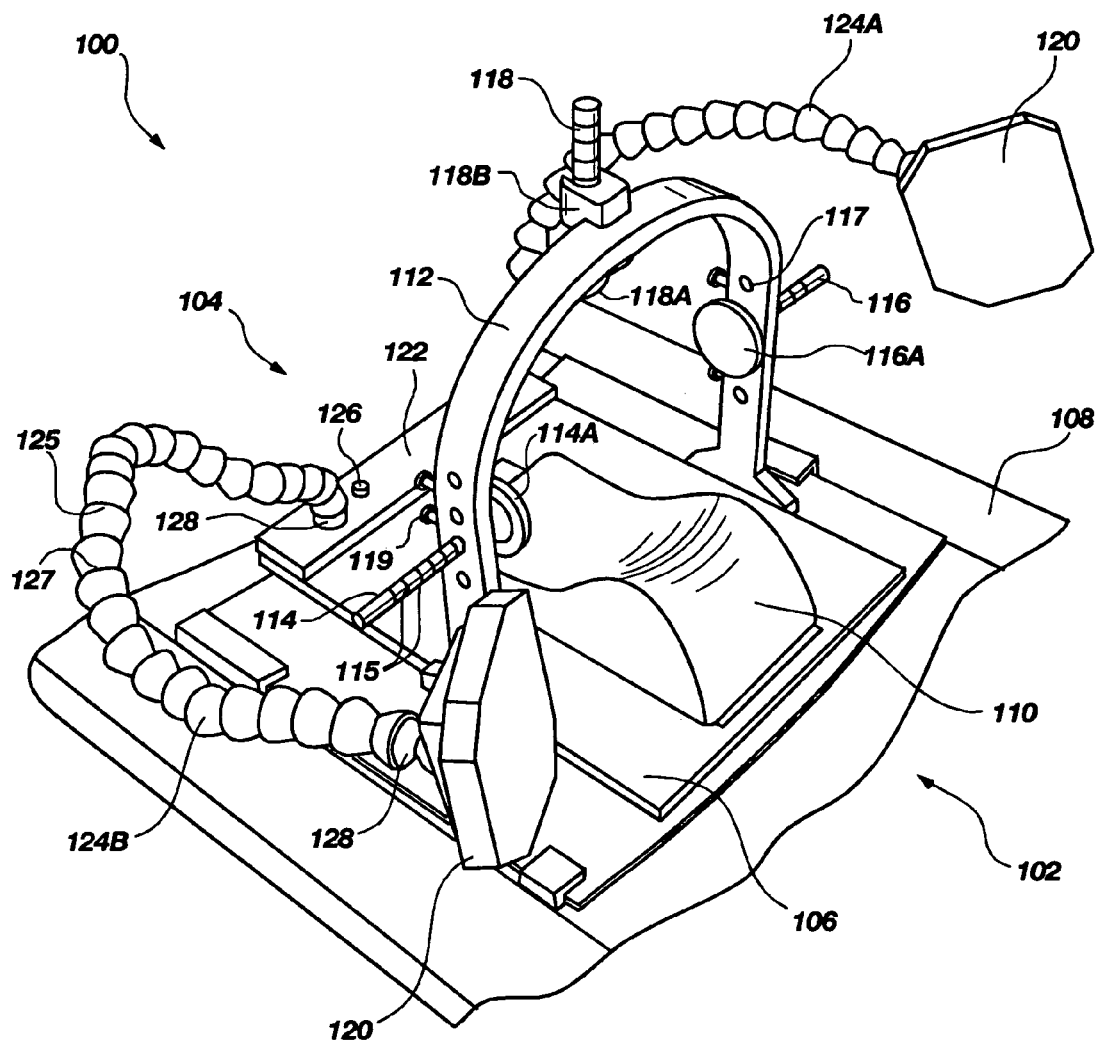
FIG. 2 depicts a perspective view of one illustrative embodiment of a system 100 in accordance with the principles of the present invention.

An illustrative embodiment of a system in accordance with the present invention is illustrated in FIG. 2. As depicted, system generally 100 comprises an anatomical positioning device for the head and neck generally 102 and a modular set of positionable imaging elements generally 104. The anatomical positioning device for the head and neck generally 102 includes a base plate 106 that, for example, snaps into and out of an imaging platform 108. Any structure required or desirable for making an attachment to an imaging platform or patient immobilization system may be included in the system 100, in accordance with the present invention. Illustrative examples of such connection structures may include rabbet edges on the base plate 106 that correspond to a mating surface around the periphery of a hole in a platform surface, beveled edges on the base plate 106, with the wider portion of the bevel at the top surface and a corresponding bevel on the edges of the opening of the platform top. It will be appreciated that any suitable structure known to those of ordinary skill in the art for attaching an insert to an imaging platform may be used. It will be further appreciated by one of skill in the art that the base plate 106 may merely be placed upon the imaging platform and clamped or screwed thereto, or held in place by the weight of a subject when placed thereon. Where the imaging platform includes alignment features, such as alignment lines or lights, corresponding alignment markings may be disposed on the base plate 106.

The anatomical positioning device for the head and neck generally 102 further includes an adjustable head support 110 that preferably fits into a slot in the base plate 106. The slot in base plate 106 and head support 110 are configured such that head support 110 may slide freely in slot and thus be positionable about the length of base plate 106. Arch 112 may be positioned about the length of the base plate 106 through the use of multiple mounting posts for arch 112 or by providing a slot for arch 112 in a manner similar to that for head support 110. Arch 112 holds right and left stabilization posts 114 and 116, respectively, each of which ends in enlarged padded end pieces 114A and 116A for placement against the head of a patient. Similarly, in the depicted embodiment, nasium stabilization post 118 placed at the top of the arch 112 ends in a nasium disk 118A, which contacts the bridge of the nose of a subject during use (see, FIG. 4). The positions of the right, left and nasium stabilization posts 114, 116, and 118, are all preferably indexable by the measurement markings thereon, such as measurement marking 115 on right stalibilzation post 114. Head support 110, and arch 112 are similarly indexable. Such indexing allows an operator to record the position of each of these elements so that they can be precisely reset if there is ever any need to remove the patient from the system. The ability to precisely reset these elements further allows for precise repositioning of a subject so that comparable images may be taken over a period of time.

As depicted, stabilization posts 114, 116 may pass through the body of the arch 112, and be adjustably retained by screws 119. Alternatively, clamps or locks located in the body of the arch 112 may be used, or the posts may be threaded and be received by corresponding threaded apertures in the arch 112. Stabilization post 118 may pass through some support structure such as illustrated by 118B, attached to arch 112 or directly through a corresponding aperture in the arch 112. The position of stabilization post 118 may be retained within support structure 118B by a thumb screw 119. Alternatively, clamps or locks located in the body of the arch 112 may be used, or the post may be threaded and be received by corresponding threaded apertures in the arch 112. Arch 112 may include multiple positions for receiving the stabilization posts 114, 116 and 118, such as those represented at numeral 117 in order to allow for use of the system with different sized subjects. It will be appreciated that any suitable retaining system known to those of ordinary skill in the art may be used to retain stabilization posts 114, 116, and/or 118 in the desired position.

Positioning a subject in the anatomical positioning device for the head and neck generally 102 includes placing the head of the subject on adjustable head support 110 and then adjusting the position of adjustable head support 110 such that nasium disk 118A will sit firmly on the bridge of the subject's nose. Stabilization post 118 is then lowered bringing nasium disk 118A into operative contact with the nose of the subject. If necessary, the position of arch 112 may be adjusted so as to achieve optimal placement of nasium disk 118A on the nose of the subject. Stabilization posts 114 and 116 are then positioned in one of the possible positions 117 for receiving the stabilization posts and then stabilization posts 114 and 116 are extended such that enlarged padded end pieces 114A and 116A are placed in operative contact with head of the subject. The position of each element may then be indexed using the markings disposed thereon. As would be apparent to one of skill in the art, the exact order by which the elements are brought into contact with the head of the subject is unimportant so long as they are each eventually adjusted to immobilize the head and neck.

Where possible, the anatomical positioning device for the head and neck generally 102 may be manufactured by adapting commercially available positioning devices for radiation therapy treatment. For example, suitable components from MED-TEC of Orange City, Iowa may be used as base plate 106, arch 112, head support 110 and the stabilization posts. Modifications to commercially available components, including adding a connecting interface to allow base plate 106 to interface with imaging platform 108 may be utilized. Other alterations may include those for increased patient comfort and reproducibility of positioning. For instance, the left and right stabilization posts 114 and 116, and the adjustable head support 110 may be made indexable and padded. Similarly, different sizes of nose disks may be adapted for used for use on nasium stabilization post 118.

Figure 3:
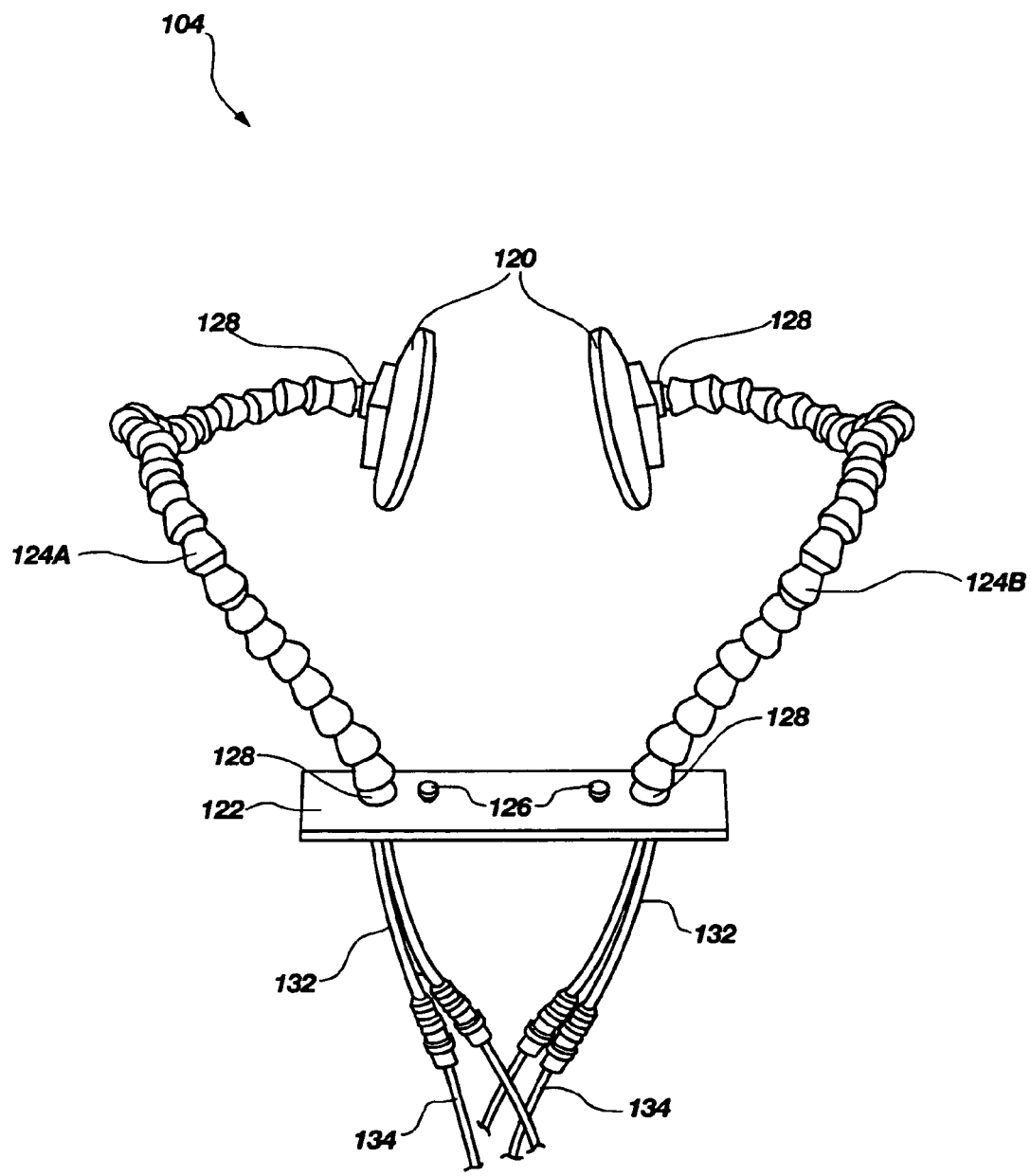
FIG. 3. depicts a modular set of positionable imaging elements

FIG. 3 depicts a modular set of positionable imaging elements generally 104 separate from device 100. Each system 100 may include multiple positionable imaging elements generally 104 with different imaging elements 120 for different uses. The modular set of positionable imaging elements generally 104 comprises one or more imaging elements 120 which may be attached to a removable plate 122 via a linking system exemplified by, for example, flex pipes 124A and 124B. Although MRI coils are the present preferred imaging elements 120, one of skill in the art would appreciate that MRI coils are but one example of an imaging element in accordance with the present invention. Any imaging element 120 designed to emit or receive electromagnetic radiation or magnetic fields in such a way so as to help provide an internal image of a subject may be used as an imaging element. Examples of suitable imaging elements include, but are not limited to: x-ray emitters, x-ray detectors, MRI coils, magnets, radio wave emitters, radio wave detectors, ultrasound emitters, ultrasound detectors, radiation detectors, gamma-ray detectors, and radiation emitters.

Flex pipes 124A and 124B may be a flexible hollow pipe made from an injected molded plastic or other polymer that is designed to retain adjustment into a desired position. For example, as depicted, flex pipes 124A and 124B have enlarged areas 125 adjacent to bending points 127, which allow the pipe to bend into a desired shape, that is then maintained. As will appreciated by one of skill in the art, the use of flex pipes 124A and 124B is merely exemplary of the linking systems that may be used to link the imaging elements to the removable plate 122. Different systems for linking imaging elements to removable plate 122, include, but are not limited to, rigid and non-rigid systems. Examples of rigid systems include but are not limited to solid or hollow plastic or metal structures, such as a supporting framework which allows for adjustment of a retained imaging element to a desired position. Examples of non-rigid systems include, but are not limited to flex pipe, bendable wire or cable, articulatable tubing or rods, and other adjustable means of supporting imaging elements 120.

Removable plate 122 may be attached to the base plate 106 such that the modular set of positionable imaging elements generally 104 attached to the base plate 106 may be easily removed and interchanged with another set of imaging elements according to the needs of the operator. Attachment may be accomplished with one or more attachment elements that interact with corresponding structures on the base plate 106. For example, the depicted thumb screws 126 may be received by a corresponding threaded opening in the base plate 106, although any other suitable attachment system may be used. Examples of suitable attachment systems include, but are not limited to, thumb screws, pull down catches, hooked loop catches, spring hook catches, compression spring pull down catches, rotating catches, pin latches, mechanical seating, friction fitting, slots, pockets, magnets and magnetic latches, or any other structure for retaining removable plate 122 to base plate 106.

The imaging elements 120 and removable plate 122 are attached to flex pipe 124 via connectors 128, which are depicted as hollow pivot joints. It will be appreciated that the use of pivot connectors 128 is merely exemplary of one type of connector 128 that may be used to attach imaging elements 120 and removable plate 122 to the linking system represented by flex pipe 124. It will be further appreciated that imaging elements 120 and removable plate 122 may be attached to the linking system represented by flex pipe 124 by different means.

Figure 4:
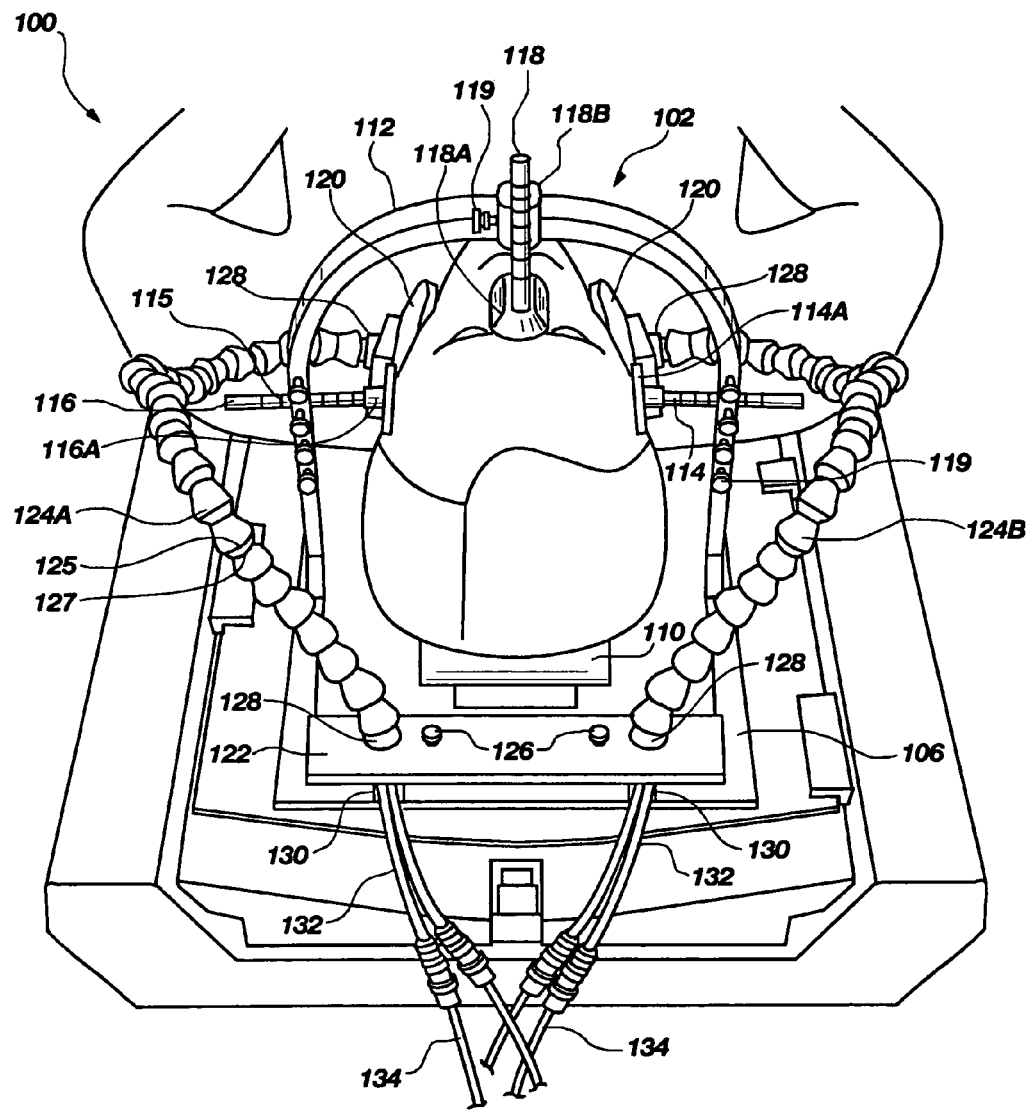
FIG. 4 depicts the embodiment of FIG. 1 with a subject positioned thereon.

FIG. 4 depicts the embodiment of FIG. 2 with a subject in place therein. More clearly visible in this view are removable plate 122 and thumb screws 126 of the modular set of positionable imaging elements generally 104. Also visible are channels 130 which are cut into base plate 106. In the exemplary embodiment shown, channels 130 allow imaging element leads 132 to pass from underneath removable plate 122 and attach to operating leads 134 to allow the powering of the imaging elements. Where the imaging element leads 132 do not pass through the center of the linking system represented by flex pipe 124 the existence of channel 130 may not be required.

Systems in accordance with the present invention may be used for medical imaging. An image may be acquired as outlined in the flowchart of FIG. 5. As depicted therein, an anatomical positioning system in accordance with the present invention, such as anatomical positioning device for the head and neck 102, that is capable of immobilizing the portion of the subject to be imaged is selected based upon the anatomical portion of the subject that is to be imaged (depicted at S1). If desired or appropriate, the anatomical positioning system may then be mounted or attached to an imaging platform (depicted at S2). The portion of the subject to be imaged is immobilized using the anatomical positioning system, such as through the use of head support 110, arch 112, and stabilization posts 114, 116, and 118 (depicted at S3). One or more modular imaging elements, such as positionable imaging elements 104, are selected according to the needs of the imaging operation (depicted at S4). If desired, the positions of any indexable elements that are part of the anatomical positioning system, such as head support 110, arch 112, and stabilization posts 114, 116, and 118, are recorded to allow precise repositioning of the subject at a later time. (depicted at S5) The one or more modular imaging elements, such as positionable imaging elements 104, are attached to the anatomical positioning system, such as anatomical positioning device for the head and neck 102, and positioned as needed for acquiring the image (depicted at S6). An image is then acquired using the imaging elements and any additional associated equipment, such as a controlling computer system, and electromagnetic receiving or emitting devices (depicted at S7). The acquired image may constitute a "scanning pass" comprising of multiple images taken in a single session.

If a second or subsequent image (or imaging pass) is required, for improvement of the image, suitability for use in planning or providing treatment or diagnosis, or for comparison, the one or more imaging elements, such as imaging elements 120, may then be repositioned to acquire a new image (depicted at R1 and S7). Where a different set of one or more imaging elements are desired to be used, a different set of imaging elements, such as positionable imaging elements 104, may be substituted for the previous elements, by removing the replaceable plate 122 (FIG. 3) or by changing the imaging elements at connectors 128 (depicted at N1 through N4). New images may then be acquired as discussed previously herein. The subject may remain immobilized in the anatomical positioning system while the imaging elements are exchanged as the elements may be quickly replaced and positioned. Any number of images using any number of interchangeable imaging elements or element positions may be used to image a subject. When the operator is finished imaging the subject, the subject may then be removed from the anatomical positioning device or remain immobilized therein for stereotactic purposes (depicted in P1). As will be appreciated by one of skill in the art, certain steps of the method outlined in FIG. 5 may be omitted or rearranged without departing from the scope of the present invention.

Once being appraised of the invention, one of skill in the art will be able to make it. As previously mentioned, existing products may be modified to make the present inventions, and many of the items are "off the shelf."

To further illustrate the present invention without limiting it, the following illustrative examples are provided., which show that embodiments of systems and methods of the present invention, provide consistent anatomical positioning of a subject and imaging elements. In these experiments, volunteer subjects were scanned with a large field of view using a very low resolution MOTSA (multiple overlapping thin-slab acquisition) imaging sequence to form MRI images of the carotid arteries.

Collected image data was used to calculate the three-dimensional rigid body head translation Vectors and rotation angles from fiducial markers that had been placed on the volunteer's head. The vessels were then segmented using Dennis Parker's ZBS algorithm and the vessel center-point locations were calculated for the vessels in every axial slice. The relative shift from the reference data in the x and y directions or the left/right and anterior/posterior directions were computed for each slice.

EXAMPLE I

Figure 5:
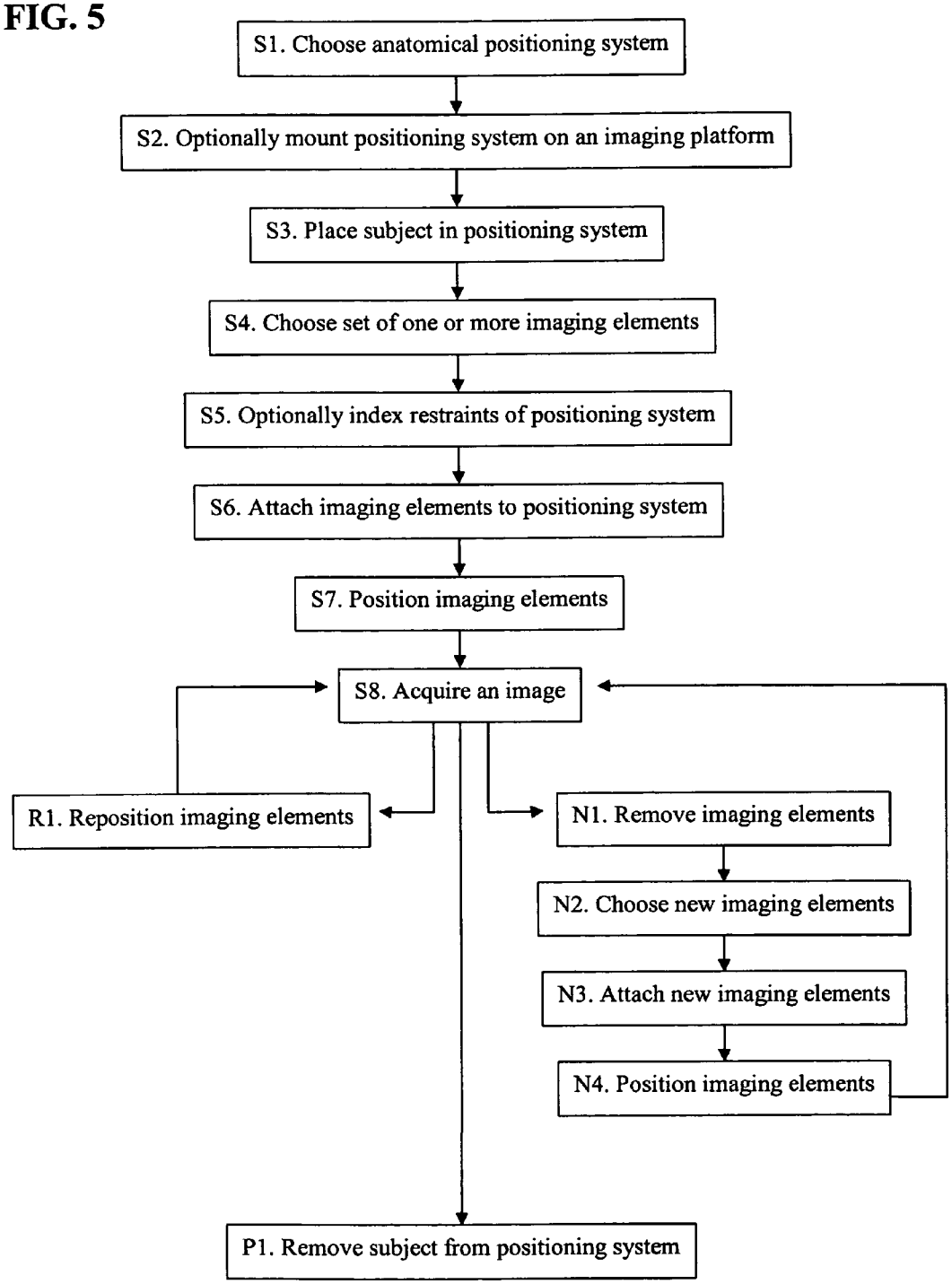
FIG. 5 depicts a flow chart of one illustrative embodiment of acquiring an image in accordance with the principles of the present invention.

MRI Images of Carotid Arteries Acquired Without Using the Restraints of the Anatomical Positioning Device In the first example, the subject was imaged using the device depicted in FIG. 2 in an anatomically correct position without using right and left stabilization posts 114, 116, or nasium stabilization post 118 (as depicted in FIG. 5, S1 through S8). This image was used as a reference scan. Then, without using left and right stabilization posts 114, 116, or nasium stabilization post 118, the subject turned his or her head varying degrees of right, left, up, and down. Images were acquired at each head rotation for comparison with the reference scan.

Figure 6:
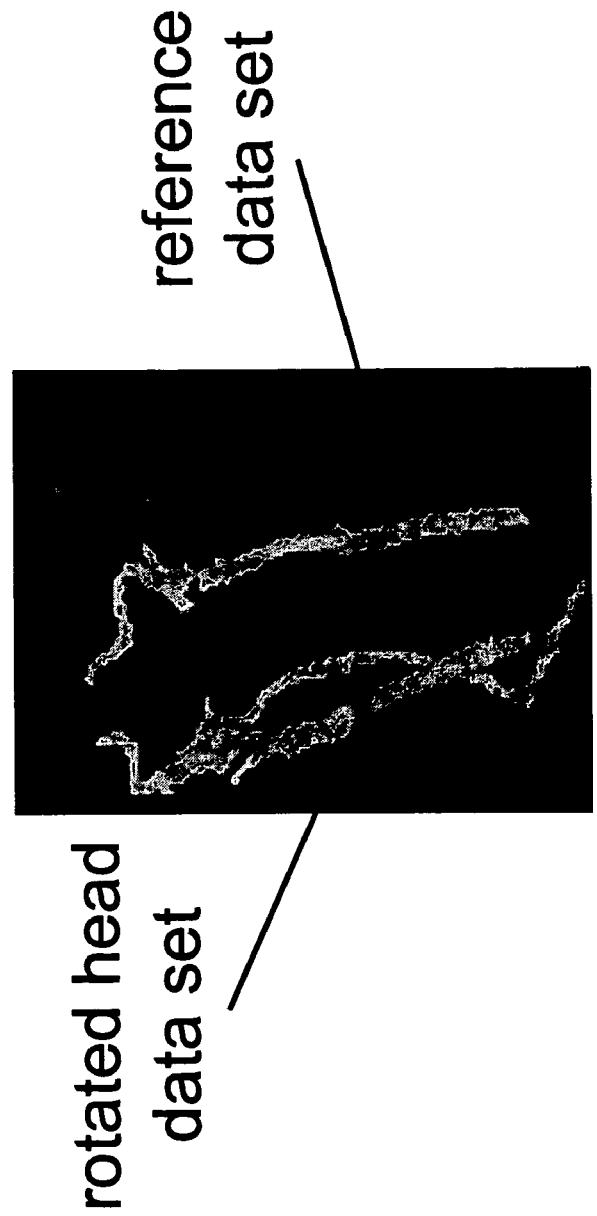
FIG. 6 depicts the segmented reference data obtained from MRI images acquired without using the stabilization posts of system 100.

FIG. 6 shows the segmented reference data plotted with the segmented rotated data. As shown in FIG. 6, the vessels move less at the aortic arch than they do towards the head.

Figure 7:
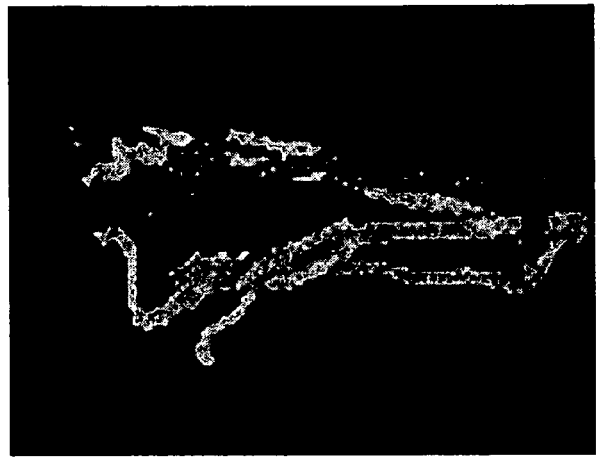
FIG. 7 depicts a rotated view of the same data set as shown in FIG. 5.

FIG. 7 shows a rotation of the same data set as shown in FIG. 6. In FIG. 7, one can see more clearly that the rotation is caused by turning the head to the right. These rotation angles are not likely to occur on an MRI table; however, this case provides a good example of the kinds of changes the successive images are attempting to visualize.

Figure 8:
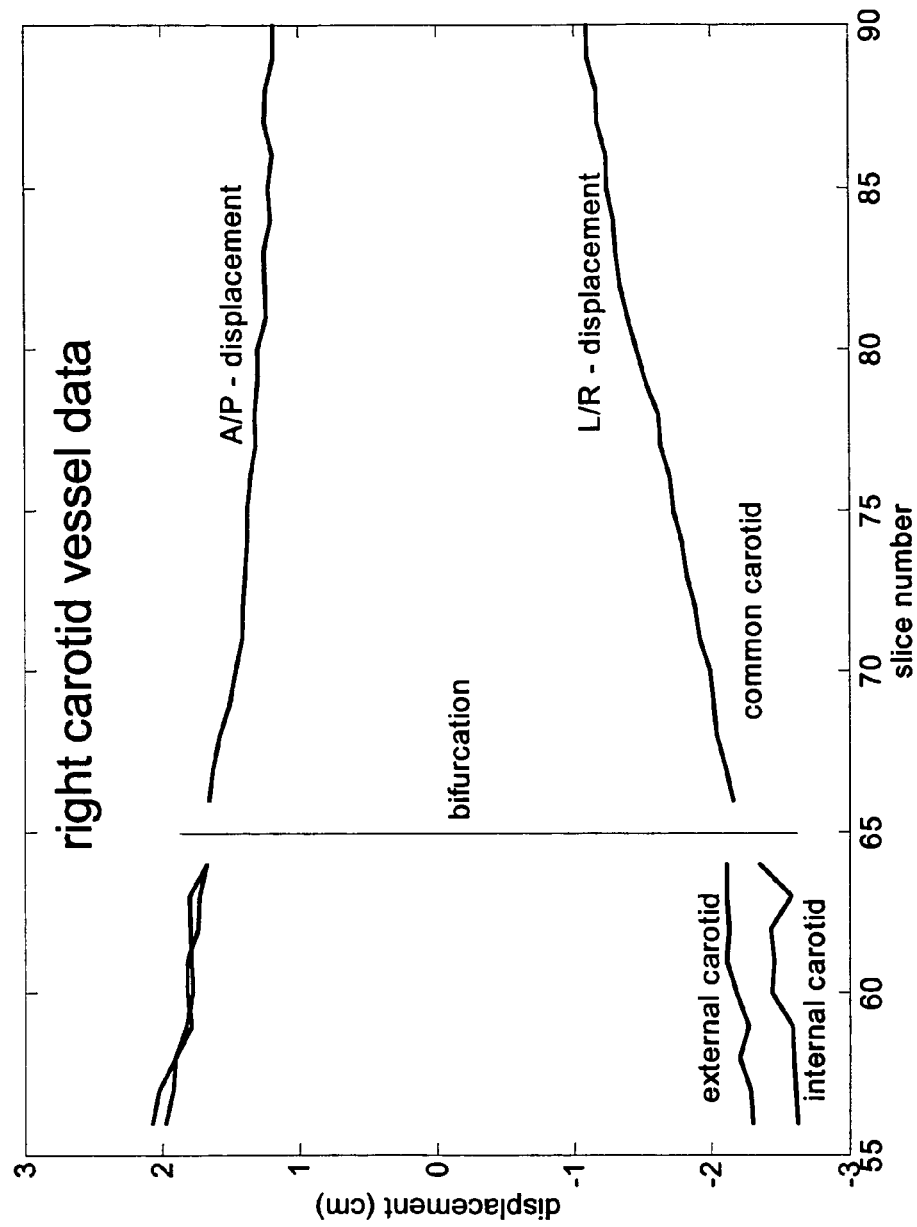
FIG. 8 depicts displacement plots for anterior-posterior and left-right displacements of the vessel in each slice along the length of the vessel for the data obtained from MRI images acquired without using the stabilization posts of system 100.

FIG. 8 shows displacement plots for anterior-posterior and left-right displacements of the vessel in each slice along the length of the vessel in the first experimental example. The errors in these displacements are due to the accuracy in the segmentation algorithm. This is a significant vessel shift for this particular head rotation, and the question still remains as to how much this change in vessel position actually changes vessel morphology and how blood flow dynamics are affected.

EXAMPLE II

Figure 9:
FIG. 9 depicts the segmented reference data obtained data obtained from MRI images acquired using the stabilization posts of system 100.

MRI Images of Carotid Arteries Acquired Using the Restraints of the Anatomical Positioning Device In the second example, the reference scan was acquired with right and left stabilization posts 114, 116 and nasium stabilization post 118 of the device of FIG. 2 in place (as depicted in FIG. 5, S1 through S8). The volunteer was asked to rotate his or her head in all four directions as far as possible without causing any pain and images were acquired at the limits of those rotations FIG. 9 shows the results of the second experimental example. In the second example, the volunteer tried to move within the constraints of a system 100 according to the present invention and was able to obtain a 2.4 degree turn. Visible from the segmented data in FIG. 9 is that these small rotation angles did not result in much vessel movement or displacement compared to the reference data set.

Figure 10:
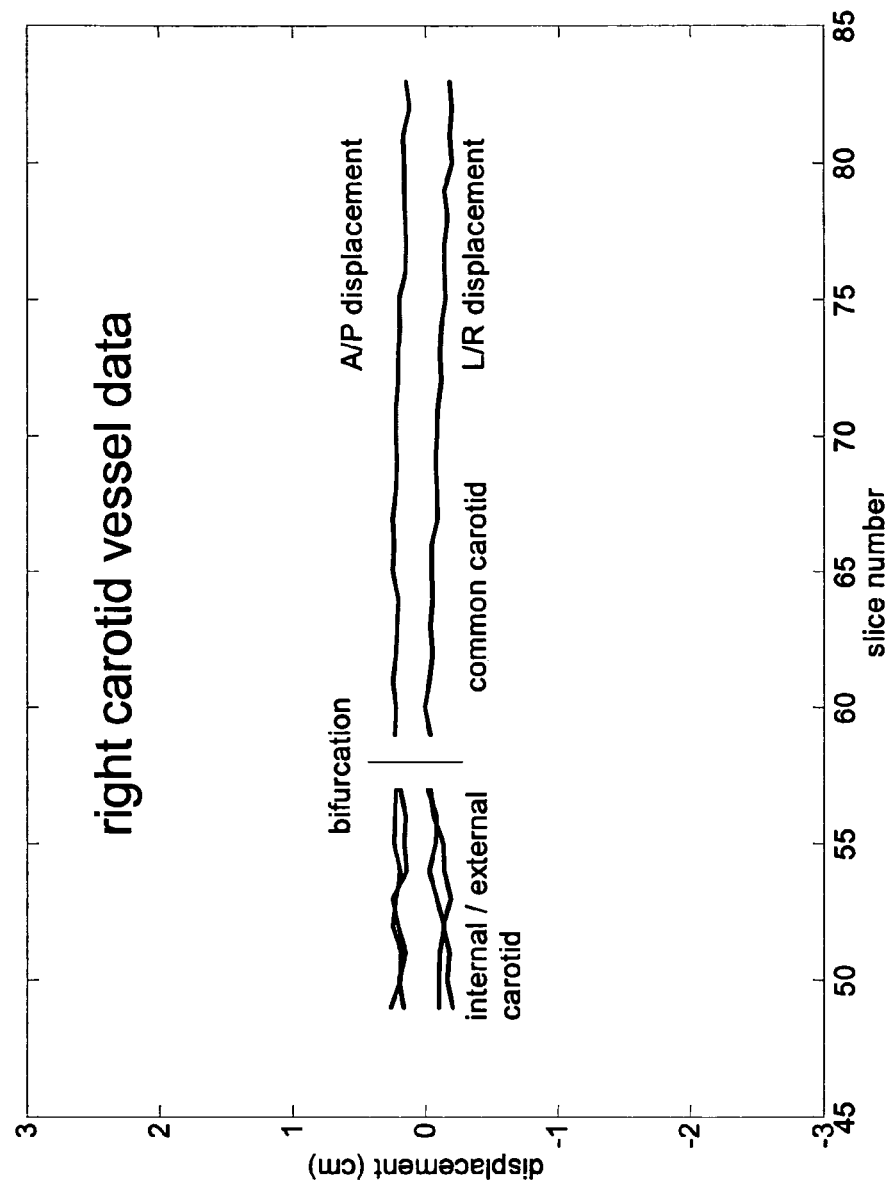
FIG. 10 depicts displacement plots for the data obtained data obtained from MRI images acquired using the stabilization posts of system 100.

FIG. 10 shows displacement plots for the data obtained in the second example where it is shown that the vessels were not displaced more than a few millimeters from the reference data.

EXAMPLE III

MRI Images of Carotid Arteries Acquired after Removing the Subject from the Anatomical Positioning Device and then Repositioning the Subject in the Anatomical Positioning Device The third example comprised obtaining a reference scan using all aspects of system 100 (i.e., with right and left stabilization posts 114, 116 and nasium stabilization post 118 in place) as depicted in FIG. 5, S1 through S8, followed by having the subject get up off the imaging platform 108, remove system 100 from the imaging platform 108. The positioning of the subject on the imaging platform 108 was then repeated, in order to simulate a repositioning of a subject for actual imaging in a system according to the present invention (as depicted in FIG. 5, S1 through S8).

Figure 11:
FIG. 11 depicts the segmented reference data obtained data obtained from MRI images acquired after the removal and subsequent repositioning of the subject.

FIG. 11 shows the results of the third experimental example. In this particular example, an attempt was made to place the volunteer back on the table in the same position as in the previous scan. These small rotation angles indicate that good reproducibility was achieved, as there is very little misalignment between the segmented data sets.

Figure 12:
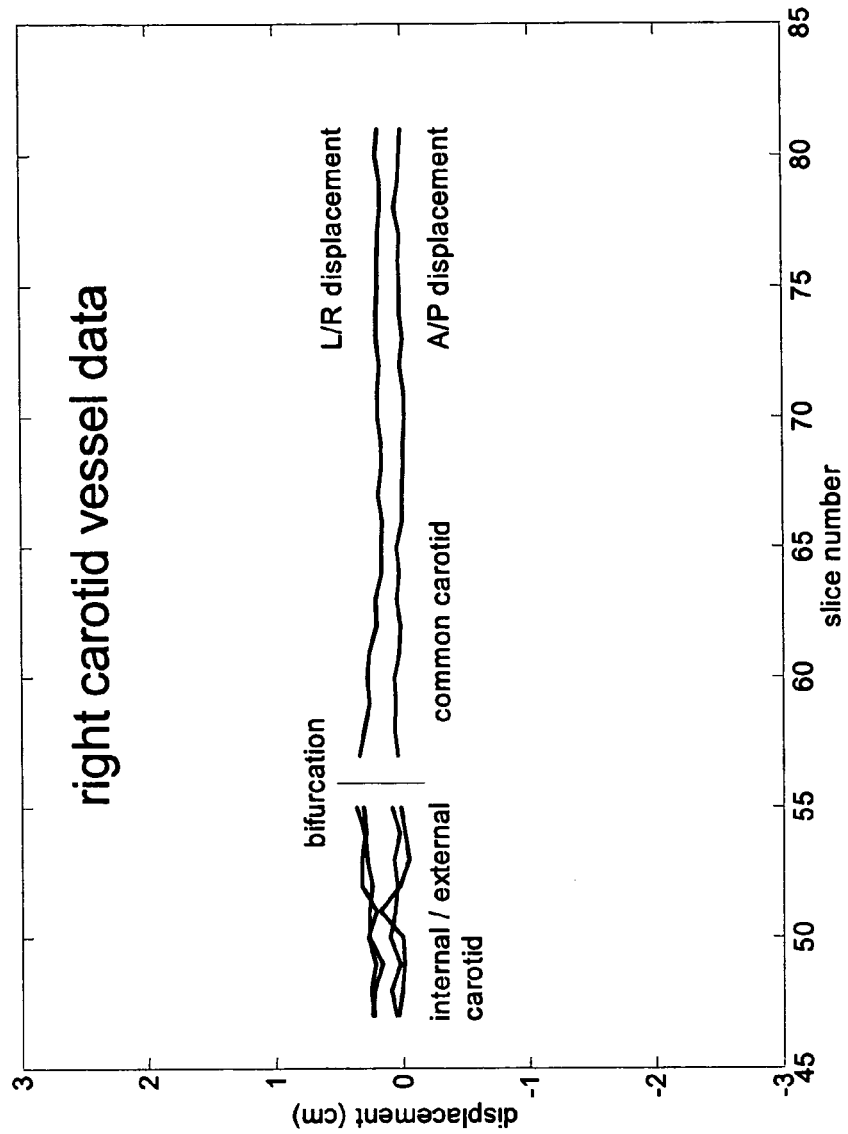
FIG. 12 depicts displacement plots for the reference data obtained data obtained from MRI images acquired after the removal and subsequent repositioning of the subject.

FIG. 12 shows displacement plots for the data obtained in the third example. The vessel is only changing position by a few millimeters and most misalignment is in the left-right direction.

These experimental examples show that system 100 may be used according to the principles of the invention to consistently position a subject's head within a few degrees of the reference position. With careful techniques, one can reposition the carotid vessels within a several mm tolerance between different subject imaging studies.

While this invention has been described in certain embodiments, the present invention can be further modified with the spirit and scope of this disclosure. This application is therefore intended to cover any variations, uses, or adaptations of the invention using its general principles. Further, this application is intended to cover such departures from the present disclosure as come within known or customary practices in the art to which this invention pertains and which fall within the limits of the appended claims.

What is claimed is:

1. A system for acquiring an image of a subject, said system comprising:
   a retention system for retaining the subject in a desired position for medical imaging of a head and neck of the subject; and
   at least one imaging element attached to a distal end of a variable position linking system attached to the retention system, the at least one imaging element and variable position linking system being positioned external the subject;
   wherein the at least one imaging element is attached to the distal end of the variable position linking system by a connector configured to allow positioning of the imaging device independent of the variable position linking system;
   wherein the system for anatomically positioning the subject comprises a base plate and an arch comprising a first attachment end and a second attachment end, the first and second attachment ends configured to be attached to an imaging platform.

2. The system of claim 1, wherein the variable position linking system is connected to a plate that is releasably attached to the retention system.

3. The system of claim 1, wherein the at least one imaging element is selected from the group consisting of x-ray emitters, x-ray detectors, MRI coils, magnets, radio wave emitters, radio wave detectors, ultrasound emitters, ultrasound detectors, radiation detectors, gamma-ray detectors, and radiation emitters.

4. The system of claim 1, wherein the variable position linking system comprises flex pipe attached to the at least one imaging element and to the retention system.

5. The system of claim 4, wherein electrical leads for powering the imaging element pass through an interior portion of the flex pipe.

6. The system of claim 1, wherein the base plate comprises an attachment structure for attachment of the base plate to an imaging platform.

7. The system of claim 1, further comprising a stabilization element disposed on the arch for interaction with the head of the subject disposed in the positioning system.

8. The system of claim 7, wherein the stabilization element is selected from the group consisting of a right stabilization element, a left stabilization element, and a nasium stabilization element.

9. The system of claim 7, wherein the stabilization element comprises an indexable post and an enlarged contact member for contacting the head of the subject disposed in the positioning system.

10. The system of claim 1, wherein the at least one imaging element is removably attached to the retention system.

11. The system of claim 1, wherein the at least one imaging element is removably attached to the retention system by removal of the variable position linking system from the retention system.

12. The system of claim 11, wherein removal of the variable position linking system from the retention system may be effectuated by removal of a plate connected to the variable position linking system from the retention system.

13. A method of imaging a subject comprising:
    positioning the subject on a system for consistent anatomical positioning of the subject's head and neck;
    selecting at least one removably attachable imaging element, said imaging element being attached to a distal end of a variable position linking system by a connector configured to allow positioning of the imaging device independent of the variable position linking system;
    attaching the at least one removably attachable imaging element and variable position linking system to the system for consistent anatomical positioning, wherein the at least one imaging element and variable position linking system are positioned external the subject; and
    acquiring an image of the subject by performing a medical imaging procedure;
    wherein positioning the subject's head and neck comprises attaching a base plate of the system for consistent anatomical positioning to an imaging platform, and positioning at feast one stabilization element disposed in an arch attached to the base plate against the head of the subject.

14. The method according to claim 13, wherein attaching the at least one removably attachable imaging element to the system for consistent anatomical positioning comprises attaching an interchangeable system from variable positioning of the at least one imaging element to the system for consistent positioning.

15. The method according to claim 14, further comprising positioning the at least one imaging element for acquiring an image of the subject.

16. The method according to claim 13, wherein positioning at least one stabilization element disposed in an arch attached to the base plate against the head of the subject comprises adjusting an indexable stabilization element and recording the position of the indexable stabilization element.

17. The method according to claim 13, wherein positioning at least one stabilization element disposed in an arch attached to the base plate against the head of the subject comprises positioning at least one stabilization element selected from the group consisting of a left stabilization element disposed on a left side of the arch, a right stabilization element disposed on a right side of the arch, and a nasium stabilization element disposed on a tope side of the arch.

18. The method according to claim 13, wherein positioning at least one stabilization element disposed in an arch attached to the base plate against the head of the subject comprises attaching the arch to the base plate.

* * * * *